United States Patent
Sato et al.

(10) Patent No.: US 9,175,317 B2
(45) Date of Patent: Nov. 3, 2015

(54) **METHOD FOR PRODUCING A POLYHYDROXYALKANOATE USING A MICROORGANISM BELONGING TO THE GENUS *CUPRIAVIDUS***

(75) Inventors: Shunsuke Sato, Takasago (JP); Tetsuya Fujiki, Osaka (JP); Keiji Matsumoto, Takasago (JP)

(73) Assignee: Kaneka Corporation, Osaka (JP)

( * ) Notice: Subject to any disclaimer, the term of this patent is extended or adjusted under 35 U.S.C. 154(b) by 19 days.

(21) Appl. No.: 13/981,728

(22) PCT Filed: Jan. 27, 2012

(86) PCT No.: PCT/JP2012/051775
§ 371 (c)(1),
(2), (4) Date: Oct. 11, 2013

(87) PCT Pub. No.: WO2012/102371
PCT Pub. Date: Aug. 2, 2012

(65) Prior Publication Data
US 2014/0057326 A1  Feb. 27, 2014

(30) Foreign Application Priority Data
Jan. 27, 2011 (JP) ................. 2011-015720

(51) Int. Cl.
*C12P 7/62* (2006.01)
*C12N 15/74* (2006.01)
*C12N 9/10* (2006.01)

(52) U.S. Cl.
CPC ............... *C12P 7/625* (2013.01); *C12N 9/1029* (2013.01); *C12N 15/74* (2013.01); *C12Y 203/01* (2013.01)

(58) Field of Classification Search
None
See application file for complete search history.

(56) References Cited

U.S. PATENT DOCUMENTS

| 5,811,272 A | 9/1998 | Snell et al. |
| 6,593,116 B1 | 7/2003 | Huisman et al. |
| 2009/0130731 A1 | 5/2009 | Maruyama |

FOREIGN PATENT DOCUMENTS

| EP | 0824148 A2 | 2/1998 |
| JP | 10-108682 A | 4/1998 |
| JP | 2008-086238 A | 4/2008 |
| WO | WO-98/04713 | 2/1998 |
| WO | WO-2006/101176 A1 | 9/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession P23608. Nov. 1, 1991.*
Accession O32471. Jan. 1, 1998.*
Accession AF314206. Mar. 21, 2001.*
Accession AR604673. Dec. 15, 2004.*
International Preliminary Report on Patentability issued Jul. 30, 2013 in Appln. No. PCT/JP2012/051775.
Q. Qi et al., "Polyhydroxybutyrate biosynthesis in *Caulobacter crescentus*: molecular characterization of the polyhydroxybutyrate synthase", Microbiology , 2001, vol. 147, p. 3353-3358.
D. Mumberg et al., Database GenBank [online], Accession No. DQ019861, Sep. 28, 2005 uploaded, Title: *Saccharomyces cerevisiae* expression vector p426GPD, complete sequence.
M. Potter et al., "Regulation of phasin expression and polyhydroxyalkanoate (PHA) granule formation in *Ralstonia eutropha* H16", Microbiology, 2002, vol. 148, p. 2413-2426.
S. Kusaka et al., "Molecular mass of poly[(R)-3-hydroxybutyric acid] produced in a recombinant *Escherichia coli*", Appl. Microbiol. Biotechnol., 47: 140-3, 1997.
S. Kusaka et al., "Microbial Synthesis and Physical Properties of Ultra-High-Molecular-Weight poly[(R)-3-hydroxybutyrate]", J. Macromol. Sci., Pure Appl. Chem., A35(2): 319-35, 1998.
S. Kusaka et al., "Properties and biodegradability of ultra-high-molecular-weight poly[(R)-3-hydroxybutyrate] produced by a recombinant *Escherichia coli*", Int. J. Biol. Macromol., 25:, 87-94, 1999.
T. Gerngross et al., "Enzyme-catalyzed synthesis of poly[(R)-(-)-3-hydroxybutyrate]: Formation of macroscopic granules in vitro", Proc. Natl. Acad. Sci. USA, 92: 6279-83, Jul. 1995.
Delamarre et al., "Comparative study of promoters for the production of polyhydroxyalkanoates in recombinant strains of *Wautersia eutropha*", Appl. Mircrobiol. Biotechnol. (2006) 71: 668-679.
Horng et al., "Enhanced polyhydroxybutyrate (PHB) production via the coexpressed *phaCAB* and *vgb* genes controlled by arabinose PBAD promoter in *Escherichia coli*", Letters in Applied Microbiology, 50 (2010) 158-167.

* cited by examiner

*Primary Examiner* — Christian Fronda
(74) *Attorney, Agent, or Firm* — Novak Druce Connolly Bove + Quigg LLP (57) ABSTRACT

The present invention provides a microorganism that synthesizes a high-molecular-weight PHA, and a method for producing a high-molecular-weight PHA, which have a productivity of at least 100 g/L. The provision is achieved by controlling the specific activity of a PHA synthase in cells of a microorganism that belongs to the genus *Cupriavidus* and is capable of producing a PHA, to 0.1 U/mg-protein at most. The microorganism and the method enable industrially efficient production of a PHA with a weight average molecular weight of at least 4,000,000.

16 Claims, 1 Drawing Sheet

METHOD FOR PRODUCING A POLYHYDROXYALKANOATE USING A MICROORGANISM BELONGING TO THE GENUS *CUPRIAVIDUS*

CROSS REFERENCE TO RELATED APPLICATIONS

This application is a National Phase filing under 35 U.S.C. §371 of PCT/JP2012/051775 filed on Jan. 27, 2012; and this application claims priority to Application No. 2011-015720 filed in Japan on Jan. 27, 2011 under 35 U.S.C. §119; the entire contents of all are hereby incorporated by reference.

TECHNICAL FIELD

The present invention relates to a microorganism producing a high-molecular-weight polyester, particularly a microorganism producing a high-molecular-weight polyhydroxyalkanoate (hereinafter, polyhydroxyalkanoate is referred to as PHA); and a method for industrially efficiently producing a PHA which includes utilizing the microorganism.

The present invention also relates to a microorganism producing an ultrahigh-molecular-weight biodegradable polyester which has excellent processability. More specifically, the present invention relates to a technology that controls the specific activity of a polyhydroxyalkanoate synthase to a level at which a high-molecular-weight polyester is produced. The technology employs a method for industrially producing an ultrahigh-molecular-weight polyester at a high yield which includes utilizing the microorganism.

BACKGROUND ART

PHAs are polyester-type organic polymer molecules produced by a variety of microorganisms. Actually, PHAs are a biodegradable thermoplastic polymer and also producible from renewable resources. Hence, some attempts have been made to industrially produce a PHA as an environmentally friendly material or biocompatible material for various industrial use.

PHAs are formed from monomer units generally called 3-hydroxyalkanoic acids which are specifically exemplified by 3-hydroxybutyric acid, 3-hydroxyvaleric acid, 3-hydroxyhexanoic acid, 3-hydroxyoctanoic acid, and 3-hydroxyalkanoic acids with a longer alkyl chain. The polymer molecules are formed by homopolymerization or copolymerization of the said 3-hydroxyalkanoic acids.

Examples of such a PHA include poly-3-hydroxybutyric acid (hereinafter abbreviated as P(3HB)) which is a homopolymer of 3-hydroxybutyric acid (hereinafter abbreviated as 3HB); a copolymer of 3-hydroxybutyric acid (3HB) and 3-hydroxyvaleric acid (hereinafter abbreviated as 3HV) (hereinafter, the copolymer is abbreviated as (3HB-co-3HV)); and a copolymer of 3HB and 3-hydroxyhexanoic acid (hereinafter abbreviated as 3HH) (hereinafter, the copolymer is abbreviated as (3 HB-co-3HH)).

Polyesters have different characteristics depending on the molecular weight. Polyesters with as high a molecular weight as possible are preferred in the case of fiber processing. Different microorganisms produce polyhydroxyalkanoates with different molecular weights ranging from 50,000 to 1,000,000 in general. Accordingly, production of a PHA with a higher molecular weight has been studied.

Non Patent Literatures 1, 2, and 3 show a production method for P(3HB) with a weight average molecular weight of higher than 10,000,000 by controlling the pH and glucose concentration in culturing of *Escherichia coli* introduced *Ralstonia eutropha*-derived genes related to PHA synthesis. These documents show that a high-molecular-weight P(3HB) has better physical properties (e.g., tensile strength and restretchability) which are important for fiber processing or others.

Non Patent Literature 4 shows that change of the PHA synthase concentration in in-vitro P(3HB) production system enables production of P(3HB) with a weight average molecular weight of 3,000,000 to 12,000,000.

Patent Literature 1 shows that in production of P(3HB) using *Escherichia coli* harboring an expression vector that contains a PHA synthase gene controlled by an inducible promoter, the amount of the enzyme expressed by the inducer enables control of the weight average molecular weight between 780,000 and 4,000,000.

Patent Literature 2 shows that expression of a PHA synthase gene integrated at different sites on a bacterial chromosome leads to production of PBAs with different molecular weights. In the case where an *Aeromonas caviae*-derived PHA synthase gene and genes producing a substrate monomer were integrated into *R. eutropha* chromosome, polyesters including 3-hydroxyhexanoate and 3-hydroxyoctanoate which has a molecular weight of 400,000 to 10 million was accumulated. Patent Literature 2, however, does not mention the productivity of this case.

There are also many study reports on production of P(3HB-co-3HH).

Patent Literature 3 shows production of P(3HB-co-3RH) with a weight average molecular weight of 5,100,000 at level of 109.2 g/L-biomass and 68.6% of polyester content after 64-hr cultivation of a transformant which is introduced a PHA synthase mutant gene derived from *A. caviae* and a 3-ketoacyl-ACP reductase gene (fabG) derived from *Escherichia coli* into *R. eutropha*, by using palm oil as an inexpensive carbon source.

The previous technologies have showed the production of high-molecular-weight P(3HB) and P(3HB-co-3HH) with a weight average molecular weight of at least 4,000,000 as described above, but employ expensive materials and have low productivity, which have been problems in achieving inexpensive industrial production of a high-molecular-weight polyester at a high yield.

CITATION LIST

Patent Literature

Patent Literature 1: U.S. Pat. No. 5,811,272
Patent Literature 2: U.S. Pat. No. 6,593,116
Patent Literature 3: WO 2006/101176

Non Patent Literature

Non Patent Literature 1: Appl. Microbiol. Biotechnol., 47: 140-3 (1997)
Non Patent Literature 2: J. Macromol. Sci., Pure Appl. Chem., A35: 319-35 (1998)
Non Patent Literature 3: Int. J. Biol. Macromol., 25: 87-94 (1999)
Non Patent Literature 4: Proc. Natl. Acad. Sci. USA, 92: 6279-83 (1995)

SUMMARY OF INVENTION

Technical Problem

The present invention aims to breed a microorganism producing a PHA with a molecular weight of at least 4,000,000 which could not always be produced with productivity adaptable to industrial use. Specifically, the present invention aims to provide an industrially efficient method for breeding a microorganism that produces a high-molecular-weight PHA at a high yield by controlling the specific activity of the enzyme involved in the PHA synthesis to a low level for producing a PHA using the microorganism.

Solution to Problem

The present inventors have made intensive studies on breeding a microorganism that produces a high-molecular-weight PHA at a high yield. As a result, the present inventors have found that genetic control of the specific activity of a PHA synthase leads to production of PHAs with various molecular weights at a high yield. Based on this finding, the present inventors have also found a method for production of a high-molecular-weight PHA. Thereby, the present invention has been completed.

The present invention features a microorganism belonging to the genus *Cupriavidus* of which the specific activity of a PHA synthase in cells is controlled to 0.1 U/mg-protein at most. The microorganism is also capable of producing a high-molecular-weight PHA at a level of at least 100 g/L of productivity.

The weight average molecular weight of the high-molecular-weight PHA in the present invention is preferably at least 4,000,000.

The microorganism of the present invention preferably has a PHA synthase gens encoding the amino acid sequence of SEQ ID NO:9 or 10, or a PHA synthase gene having at least 85% homologous sequence of SEQ ID NO:9 or 10 that has a PHA synthesis activity.

The microorganism of the present invention contains a PHA synthase gene whose promoter regulating the transcription has a nucleotide sequence of SEQ ID NO:11 or 12, or a nucleotide sequence having a sequence homology of at least 85% with either of the nucleotide sequences.

Particularly, the microorganism of the present invention belongs to the genus *Cupriavidus* capable of producing a PHA with a weight average molecular weight of at least 4,000,000 at a level of at least 100 g/L of productivity, and contains a gene encoding a PHA synthase having at least one nucleotide sequence selected from the group consisting of the following nucleotide sequences (1) to (4);

(1) a nucleotide sequence encoding the amino acid sequence of SEQ ID NO:9;

(2) a nucleotide sequence encoding a polypeptide that has a sequence homology of at least 85% with the amino acid sequence of SEQ ID NO:9 and has a polyhydroxyalkanoate synthesis activity;

(3) a nucleotide sequence encoding the amino acid sequence of SEQ ID NO:10; and (4) a nucleotide sequence encoding a polypeptide that has a sequence homology of at least 85% with the amino acid sequence of SEQ ID NO:10 and has a polyhydroxyalkanoate synthesis activity, wherein the gene encoding a polyhydroxyalkanoate synthase is controlled by at least one nucleotide sequence selected from the group consisting of the following nucleotide sequences (a) to (d) in such a way that a specific activity of the polyhydroxyalkanoate synthase in cells is 0.1 U/mg-protein at most;

(a) the nucleotide sequence of SEQ ID NO:11;

(b) a nucleotide sequence having a sequence homology of at least 85% with the nucleotide sequence of SEQ ID NO:11 and regulating gene transcription;

(c) the nucleotide sequence of SEQ ID NO:12; and (d) a nucleotide sequence having a sequence homology of at least 85% with the nucleotide sequence of SEQ ID NO:12 and regulating gene transcription.

The microorganism of the present invention is preferably *Cupriavidus necator*.

Culturing the microorganism of the present invention in the presence of a raw material utilizable by the microorganism (e.g. sugar, fat, oil and/or fatty acid) as a carbon source enables production of a high-molecular-weight PHA.

The high-molecular-weight PHA in the present invention is, particularly, P(3HB), P(3HB-co-3HV), or P(3HB-co-3HH).

The present invention also features a method for producing a polyhydroxyalkanoate with a weight average molecular weight of at least 4,000,000 which includes utilizing the above microorganism.

Advantageous Effects of Invention

The present invention enables industrially efficient production of an industrially useful high-molecular-weight PHA by using relatively inexpensive, renewable resources such as sugar, oil and fat.

DESCRIPTION OF EMBODIMENTS

Hereinafter, the present invention is described in detail.

In the case of producing PHA with *C. necator* as a host, the weight average molecular weight of the PHA is about several 100,000 to 2,000,000, and it has been difficult to produce a PHA with a molecular weight of at least 4,000,000 while retaining a high PHA productivity of at least 100 g/L in a culture medium. However, the present invention enables production of a high-molecular-weight PHA with a weight average molecular weight of at least 4,000,000 with a high productivity of at least 100 g/L.

The microorganism belonging to the genus *Cupriavidus* of the present invention has a specific activity of the PHA synthase controlled to 0.1 U/mg-protein at most and a PHA productivity of at least 100 g/L. The weight average molecular weight of a PHA produced by such a microorganism is at least 4,000,000; in fact, it is more than 4,000,000, and particularly at least 4,200,000.

The productivity of a PHA produced by the present invention is at least 100 g/L, and it actually can reach at least 110 g/L, even at least 120 g/L, and particularly at least 130 g/L.

The specific activity of the PHA synthase controlled in the present invention is preferably 0.1 g/mg-protein at most, more preferably 0.06 U/mg-protein at most, still more preferably 0.05 U/mg-protein at most, even more preferably 0.04 U/mg-protein at most, and most preferably 0.03 U/mg-protein at most. When a foreign PHA synthase gene is introduced into a host for production of a PHA and the specific activity is controlled to a value more than 0 U/mg-protein but not more than 0.1 U/mg-protein, a PHA with a weight average molecular weight of at least 4,000,000 can be produced with a productivity of at least 100 g/L-culture medium.

The PHA synthase gene may be a PHA synthase gene encoding the amino acid sequence of SEQ ID NO:9 which is naturally present in *C. necator* H16; a PHB synthase gene encoding a polypeptide that has a sequence homology of at least 85% with this amino acid sequence and has a PHA synthesis activity; a PHA synthase gene which is naturally present in *A. caviae*; or a PHA synthase gene encoding a polypeptide that has a sequence homology of at least 85% with this amino acid sequence and has a PHA synthesis activity. The sequence homology is more preferably at least 90%, and still more preferably at least 95%. For example, a PHA synthase gene encoding a PHA synthase with an amino acid sequence of SEQ ID NO:10 can be used. Also, other PHA synthase genes of course are suitable for use.

The preferred promoter, for controlling intracellular transcription, of the above PHA synthase gene is, for example, a lac promoter (hereinafter, lacP) from the Lac operon of *Escherichia coli* of SEQ ID NO:12, the transcriptional activity of which in *Cupriavidus* bacteria has not been known, or a phasin promoter (hereinafter, phaP) from the Phasin gene of the *C. necator* H16 strain of SEQ ID NO:11. Any nucleotide sequence having a sequence homology of at least 85% with the nucleotide sequence of SEQ ID NO:11 or 12 and regulating gene transcription is suitable for use in the present invention. The sequence homology is preferably at least 90%, and more preferably at least 95%. Any promoter capable of controlling the specific activity of the PHA synthase in cells to 0.1 U/mg-protein at most is suitable for use.

The PHA synthase specific activity in the present invention is measured by the method of Gerngross et al. (Biochemistry, 33, 9311-9320 (1994)). Specifically, the measuring method described in the examples can be used.

In the PHA synthesis in the present invention, any carbon source utilizable by *Cupriavidus* bacteria is usable. Preferred examples thereof include sugars (e.g. glucose, fructose, sucrose), fats and oils (e.g. palm oil, palm kernel oil, corn oil, coconut oil, olive oil, soybean oil, rape seed oil, Jatropha oil) and fractional oils thereof, and fatty acids (e.g. lauric acid, oleic acid, stearic acid, palmitic acid, and a myristic acid) and derivatives thereof.

The bacterium belonging to the genus *Cupriavidus* of the present invention may be of any species synthesizing a PHA, but is preferably *C. necator*, and more preferably *C. necator* H16. Here, mutant strains obtainable through artificial mutation of the microorganism, and mutant strains obtainable through genetic engineering of the microorganism can of course be used.

The promoter and the PHA synthase in the present invention may be present on a chromosome of the host cell or plasmid.

The PHA may be any PHA producible by a microorganism, but is preferably a PHA made by polymerization of a monomer selected from C4 to C16 3-hydroxyalkanoic acids, or a copolymer PHA made by copolymerization of monomers selected from C4 to C16 3-hydroxyalkanoic acids. Examples thereof include polyhydroxybutyrate P(3HB) made by polymerisation of a C4 3-hydroxyalkanoic acid; poly(3-hydroxybutyrate-co-3-hydroxyhexanoate) P(3HB-co-3HH) made by copolymerization of C4 and C6 3-hydroxyalkanoic acids; poly(3-hydroxybutyrate-co-3-hydroxyvalerate) P(3HB-co-3HV) made by copolymerization of C4 and C5 3-hydroxyalkanoic acids; and polyhydroxyalkanoates (PHAs) made by polymerization or copolymerization of C4 to C14 3-hydroxyalkanoic acid(s). The kind of PHA to be produced can be appropriately selected by, for example, introducing a known PHA synthesis-related gene into a *Cupriavidus* bacterium used as the host. If the specific activity of the PHA synthase is controlled to 0.1 U/mg-protein at most, the effect of the present invention can be achieved.

The culture method may be any method for culturing a microorganism with an addition of a carbon source to the culture medium regardless of the medium composition, the addition method of the carbon source, the culture scale, the aeration and agitation conditions, the culture temperature, and the culture time. Still, a culture method including continuous or intermittent addition of a carbon source to the culture medium is preferred.

In the method for producing a PHA of the present invention, the PHA is accumulated in the microorganism by the above culture method, and the PHA is collected from the cells by a known method. For example, the following method can be used. After the completion of culture, cultured cells are separated from the culture medium using a centrifuge or the like, and the cells are washed with distilled water and methanol, and then dried. From the dried cells, the PHA is extracted with an organic solvent such as chloroform. The solution containing the PHA is filtered to remove cell components, and the filtrate is mixed with a poor solvent such as methanol or hexane, so that the PHA precipitates. The mixture is further filtrated or centrifuged to remove the supernatant, and the precipitate is dried to collect the PHA.

The productivity of the microorganism cells can be measured by a known method such as absorptiometry or dry cell weight determination. The productivity of the substance produced by the microorganism can be determined by a known method such as the GC method or HPLC method. The amount of the PHA accumulated in cells can be measured by extracting the PHA from the cultured cells with an organic solvent such as chloroform, and drying the extract, in accordance with the method of Kato et al. (Appl. MicroBiol. Biotechnol., 45, 363(1996); Bull. Chem. Soc., 69, 515 (1996)).

EXAMPLES

The present invention is described in detail below based on examples which, however, are not intended to limit the scope of the present invention. Here, the overall gene manipulation can be performed in accordance with Molecular Cloning (Cold Spring Harbor Laboratory Press, (1989)). The enzyme cloning host and the like used in the gene manipulation can be purchased from the market supplier, and can be used in accordance with the instructions thereof. The enzyme may be any enzyme usable in gene manipulation.

Production Example 1

Construction of P(3HB-co-3HH) Synthase Gene Transfer Vector without a Promoter

The expression vector pCUP2EEREP149NS/171DG (PHB operon promoter in *C. necator* H16 (hereinafter, REP)+PHA synthase) described in JP 2007-259708 A, serving as a template, was subjected to PCR with primers 1 and 2 respectively represented by SEQ ID NO:1 and SEQ ID NO:2. Here, PCR was performed (1) at 98° C. for 2 minutes, and then (2) at 98° C. for 15 seconds, at 60° C. for 30 seconds, and at 68° C. for 2 minutes (25 cycles) with a polymerase KOD-plus- (product of Toyobo Co., Ltd.). A DNA fragment obtained by the PCR was terminally phosphorylated and digested with EcoRI and MunI. The resulting DNA fragment was ligated to the MunI-digested vector pCUP2 described in JP 2007-259708 A with a DNA ligase (Ligation High (product of Toyobo Co., Ltd.)), whereby a P(3HB-co-3HH) synthase gene-containing plasmid vector pCUP2/149NS171DGdP without a promoter was produced.

Production Example 2

Construction of P(3HB) Synthase Gene Transfer Vector without a Promoter

*C. necator* H16 genome as a template was subjected to PCR with primers 1 and 2 respectively represented by SEQ ID NO:1 and SEQ ID NO:2. PCR was performed (1) at 98° C. for 2 minutes, and then (2) at 98° C. for 15 seconds, at 60° C. for 30 seconds, and at 68° C. for 2 minutes (25 cycles) with a polymerase KOD-plus- (product of Toyobo Co., Ltd.). A DNA fragment obtained by the PCR was terminally phosphorylated and digested with EcoRI and MunI. The resulting DNA fragment was ligated to the MunI-digested vector pCUP2 described in JP 2007-259708 A with a DNA ligase (Ligation High (product of Toyobo Co., Ltd.)), whereby a P(3HB) synthase gene-containing plasmid vector pCUP2/phbcdP without a promoter was produced.

Production Example 3

Construction of P(3HB-co-3HH) Synthase Gene Expression Vector with lacP pCR-Blunt II-TOPO (product of Invitrogen) as a template was subjected to PCR with primers 3 and 4 respectively represented by SEQ ID NO:3 and SEQ ID NO:4. PCR was performed (1) at 98° C. for 2 minutes, and then (2) at 98° C. for 15 seconds, at 60° C. for 30 seconds, and at 68° C. for 2 minutes (25 cycles) with a polymerase KOD-plus- (product of Toyobo Co., Ltd.). The amplified fragment was terminally phosphorylated and digested with MunI. The fragment was ligated to a MunI-digested pCUP2phaCbP vector, whereby a plasmid vector pCUP2/lacP149NS171DG was produced.

Production Example 4

Construction of P(3HB-co-3HH) Synthase Gene Expression Vector with phaP

*C. necator* H16 genome as a template was subjected to PCR with primers 5 and 6 respectively represented by SEQ ID NO:5 and SEQ ID NO:6. The PCR was performed (1) at 98° C. for 2 minutes, and then (2) at 98° C. for 15 seconds, at 60° C. for 30 seconds, and at 68° C. for 30 seconds (25 cycles) with a polymerase KOD-plus- (product of Toyobo Co., Ltd.). The amplified fragment was terminally phosphorylated and digested with MunI. The fragment was ligated to a MunI-digested pCUP2/149NS171DGdP vector, whereby a plasmid vector pCUP2/phaP149NS171DG was produced.

Production Example 5

Construction of P(3HB) Synthase Gene Expression Vector with lacP

A plasmid vector pCUP2/lacPphbc was produced in the same manner as in Example 3, except that the plasmid used was pCUP2phbCdP.

Production Example 6

Construction of P(3HB) Synthase Gene Expression Vector with phaP

A plasmid vector pCUP2/phaPphbC was produced in the same manner as in Example 4, except that the plasmid used was pCUP2phbCdP.

Production Example 7

Construction of P(3HB-co-3HH) Synthase Gene Expression Vector with Wild Type Promoter The plasmid vector pJRDdTC+149NS171DG mentioned in WO 2005/098001 A was digested with EcoRI, so that a PHA operon promoter (ACP) from *A. caviae* and a PHA synthase gene fragment were obtained. This fragment was inserted at the MunI cleavage site of pCUP2, and thereby an expression vector pCUP2/ACP149NS/171DG was constructed.

Production Example 8

Construction of P(3HB) Synthase Expression Vector with *C. necator* H16 REP

*C. necator* H16 genome as a template was subjected to PCR with primers 7 and 8 respectively represented by SEQ ID NO:7 and SEQ ID NO:8. PCR was performed (1) at 98° C. for 2 minutes, and then (2) at 98° C. for 15 seconds, at 60° C. for 30 seconds, and at 68° C. for 3 minutes (25 cycles) with a polymerase KOD-plus- (product of Toyobo Co., Ltd.). The amplified fragment was terminally phosphorylated and digested with EcoRI. The fragment was ligated to a MunI-digested pCUP2 vector, whereby a plasmid vector pCUP2/RSPphbC was produced.

Experimental Example 1

Production of Transformant

Transformants containing the respective expression vectors produced in Production Examples 3 to 8 and a transformant containing the expression vector pCUP2EERBP149NS/171DG mentioned in JP 2007-259708 A were produced by an electric pulse method. The hosts into which the vectors were introduced were the *C. necator* ΔB1133 strain described in JP 2007-259708 A which is a phbC gene-disrupted strain of the *C. necator* H16 strain. The respective transformants thus produced are referred to as ΔB+pCUP2/lacP149NS171DG (Example 1), ΔB+pCUP2/phaP149NS171Dg (Example 2), ΔB+pCUP2/lacPphbC (Example 3), ΔB+pCUP2/phaPphbC (Example 4), ΔB+pCUP2/ACP149NS/171DG (Comparative Example 1), ΔB+pCUP2/REPphbC (Comparative Example 2), and ΔB+pCUP2EEREP149NS/171DG (Comparative Example 3). The gene manipulator used was Gene Pulser (from Bio-Rad), and the cuvettes used were ones with a gap of 0.2 cm (also from Bio-Rad). To each cuvette were put the competent cell (400 µl) and the expression vector (20 µl). The cuvette was placed in the pulser, and subjected to an electric pulse with an electrostatic capacitance of 25 µF, a voltage of 1.5 kV, and a resistance of 800Ω. After the pulse, the cell suspension in the cuvette was transferred to a NutrientBroth culture medium (product of DIFCO) for 3-hour shake culture at 30° C. The cells were then cultured on a selection plate (NutrientAgar culture medium (product of DIFCO) with kanamycin (100 mg/L)) at 30° C. for 2 days, so that the transformant was obtained.

Experimental Example 2

Production of PHA

The seed culture medium used contained 1 w/v % meat-extract, 1 w/v % Bacto-Trypton, 0.2 w/v % yeast-extract, 0.9 w/v % $Na_2HPO_4.12H_2O$, 0.15 w/v % $KH_2PO_4$, and $5 \times 10^{-6}$ w/v % kanamycin.

The preculture medium used contained 1.1 w/v % $Na_2HPO_4.12H_2O$, 0.19 w/v % $KH_2PO_4$, 1.29 w/v % $(NH_4)_2SO_4$, 0.1 w/v % $MgSO_4.7H_2O$, 2.5 w/v % palm W olein oil, a 0.5 v/v % solution of trace metal salts (a solution of 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$ in 0.1 N hydrochloric acid).

The polyester production culture medium used contained 0.385 w/v % $Na_2HPO_4.12H_2O$, 0.067 w/v % $KH_2PO_4$, 0.291 w/v % $(NH_4)_2SO_4$, 0.1 w/v % $MgSO_4.7H_2O$, and a 0.5 v/v % solution of trace metal salts (a solution of 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$ in 0.1 N hydrochloric acid). The carbon source used was a single carbon source of palm kernel-oil olein which is a low melting point fraction of palm kernel oil.

Glycerol stocks (50 μl each) of the respective transformants produced in Experimental Example 1 each were inoculated into the seed culture medium (10 ml) and cultured for 24 hours. The preculture medium (1.8 L) was inoculated with 1.0 v/v % of the seed culture in a 3-L jar fermenter (MDL-300 model from B.E. MARUBISHI Co., Ltd.). The culture was performed for 28 hours under the conditions of a culture temperature of 30° C., a stirring rate of 500 rpm, a ventilation volume of 1.8 L/min, and a pH controlled between 6.7 and 6.8. The pH was controlled using a 7% aqueous solution of ammonium hydroxide.

For polyester production culture, the production culture medium (6 L) was inoculated with the preculture seed (5.0 v/v %) in a 10-L jar fermenter (MDL-1000 model from B.E. MARUBISHI Co., Ltd). The culture was performed under the conditions of a culture temperature of 28° C., a stirring rate of 400 rpm, a ventilation volume of 3.6 L/min, and a pH controlled between 6.7 and 6.8. The pH was controlled using a 7% aqueous solution of ammonium hydroxide. The culture was performed for about 65 hours. After the culture, the cells were collected by centrifugation, washed with methanol, freeze-dried, and weighed to determine the dry cell weight.

To the obtained dry cells (about 1 g) was added chloroform (100 ml). The mixture was stirred at room temperature for one whole day and night, and the polyester in the cells was extracted. The extracted solution was filtered to remove cell residues, and concentrated in an evaporator to a total volume of about 30 ml. To the concentrated solution was gradually added hexane (about 90 ml), and the mixture was left to stand for one hour with slow stirring. The polyester thus precipitated was filtered off, and vacuum-dried at 50° C. for three hours. The dried polyester was weighed to calculate the amount of the polyester produced. The results are shown in Table 1.

TABLE 1

| Example No. | Strain | Promoter | PHA productivity(g/L) |
|---|---|---|---|
| Example 1 | ΔB + pCUP2/lacP149NS171DG | lacP | 143 |
| Example 2 | ΔB + pCUP2/phaP149NS171DG | phaP | 141 |
| Example 3 | ΔB + pCUP2/lacPphbC | lacP | 140 |
| Example 4 | ΔB + pCUP2/phaPphbC | phaP | 132 |
| Comparative Example 1 | ΔB + pCUP2/ACP149NS/171DG | ACP | 138 |
| Comparative Example 2 | ΔB + pCUP2/REPphbC | REP | 128 |
| Comparative Example 3 | ΔB + pCUP2EEREP149NS/171DG | REP | 135 |

Experimental Example 3

Analysis of Weight Average Molecular Weight (Mw) of Polyester

Figure 1:
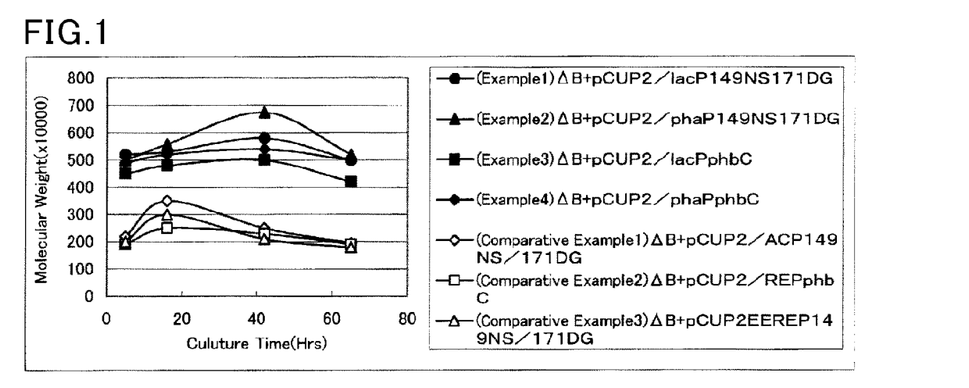
FIG. 1 is a view showing culture times of various transformants and weight average molecular weights (Mw) of accumulated polyesters in Example 9 of the present invention.

The molecular weights of the respective transformants cultured in Experimental Example 2 were measured. The weight average molecular weights (Mw) of the respective polyesters were analyzed by the gel permission chromatography method. Each extracted polyester (about 15 mg) was dissolved in chloroform (10 ml), and the solution was filtered with a 0.2-μm filter to give a measurement sample. An amount of 0.05 ml of the sample was used for analysis. The measurement system used was SLC-10A (product of SHIMADZU CORPORATION), the column used was two Shodex GPG K-806L columns (product of Showa Denko K.K.) connected in series, and the measurement temperature was 40° C. The moving phase was chloroform (1.0 ml/min), and an RI detector (RID-10A, product of SKIMADZU CORPORATION) was used. The standard samples used were polystyrenes treated in the same manner (products of Showa Denko K.K., weight average molecular weights: about 7,000,000, about 1,070,000, 150,000, 30,000), and the weight average molecular weights of the polyesters were determined from the calibration curve. The results are shown in FIG. 1.

Experimental Example 4

Measurement of Specific Activity of PHA Synthase

The specific activity of the PHA synthase was measured by the following method.

The culture broth obtained by culture in Experimental Example 1 (2 ml) was centrifuged at 4° C. and 10,000×g, for 1 minute to collect the cells. The collected cells were washed with a buffer solution (0.5 M potassium phosphate buffer) twice, and suspended in 1 ml of the same buffer solution. The suspension thus obtained was subjected to sonication to disrupt the cells, and centrifuged at 4° C. at 15,000×g for 5 minutes. The resulting supernatant was taken as a crude enzyme solution.

Figure 2:
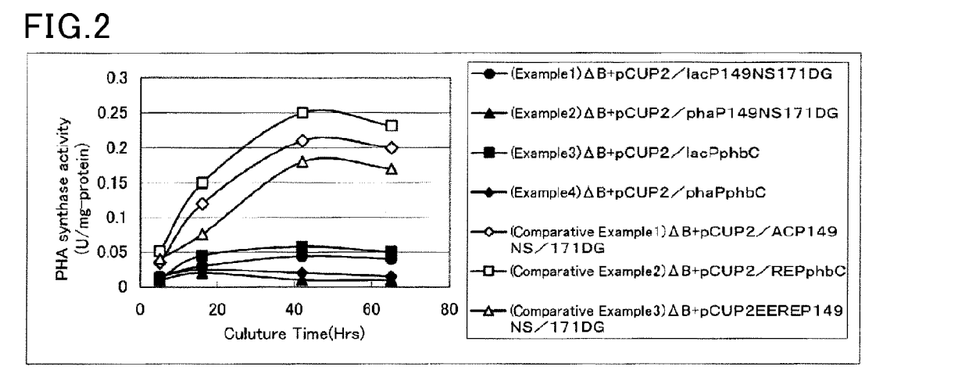
FIG. 2 is a view showing culture times of various transformants and PHA synthase specific activities in cells in Example 10 of the present invention.

The specific activity of the PHA synthase was calculated by measuring the released CoA, specifically by the method of Gerngross et al. (Biochemistry, 33, 9311-9320 (1994)). The amount of protein was determined by the Bradford method using a Bio-Rad Protein Assay (product of Bio-Rad) with bovine serum albumin as a standard. The results are shown in FIG. 2.

Experimental Example 5

3HH Composition Analysis

The 3HH composition of the polyesters produced by the respective transformants was determined by gas chromatography in the following manner. The dried polyester (about 20 mg) was mixed with a sulfuric acid/methanol mixture (15:85, 2 ml) and chloroform (2 ml), and sealed in a vessel. The mixture was heated at 100° C. for 140 minutes, so that a methyl ester, a polyester decomposition product, was obtained. The methyl ester was cooled, and sodium hydrogencarbonate (1.5 g) was gradually added to the cooled methyl ester for neutralization. This mixture was left to stand until carbon dioxide gas production stopped. To the mixture was added diisopropyl ether (4 ml), and the resulting mixture was stirred thoroughly, followed by centrifugation to give a supernatant. The monomer unit composition of the polyester decomposition product in the supernatant was determined by capillary gas chromatography. The gas chromatograph was GC-17A produced by SHIMADZU CORPORATION, and the capillary column was NEUTRA BOND-1 produced by GL Sciences Inc. (column length: 25 m, column inner diameter: 0.25 mm, liquid membrane thickness: 0.4 μm). The carrier gas was helium, the column inlet pressure was 100 kPa, and the sample was used in an amount of 1 μl. The temperature was increased from an initial temperature of 100° C. to 200° C. at a rate of 8° C./min, and further increased from 200° C. to 290° C. at a rate of 30° C./min. The analysis under the above conditions show that the PHAs produced by the transformants ΔB+pCUP2/lacP149NS171DG, ΔB+pCUP2/phaP149NS171DG, ΔB+pCUP2/ACP149NS/171DG, and ΔB+pCUP2EEREP149NS/171DG (transformants containing a PHA synthase gene encoding the PHA synthase of SEQ ID NO:10) were P(3HB-co-3HH). The results also show that the transformants ΔB+pCUP2/lacPphbC, ΔB+pCUP2/phaPphbC, and ΔB+pCUP2/REPphbC (transformants containing a PHA synthase gene encoding the PHA synthase of SEQ ID NO:9) produced P(3HB) without the 3HH monomers.

The invention claimed is:

1. A microorganism belonging to the genus *Cupriavidus* which is capable of producing a polyhydroxyalkanoate with a weight average molecular weight of at least 4,000,000 at a level of at least 100 g/L of productivity, the microorganism comprising
    a gene encoding a polyhydroxyalkanoate synthase having at least one nucleotide sequence selected from the group consisting of the following nucleotide sequences (1) to (4):
    (1) a nucleotide sequence encoding the amino acid sequence of SEQ ID NO:9;
    (2) a nucleotide sequence encoding a polypeptide that has a sequence homology of at least 95% with the amino acid sequence of SEQ ID NO:9 and has a polyhydroxyalkanoate synthesis activity;
    (3) a nucleotide sequence encoding the amino acid sequence of SEQ ID NO:10; and
    (4) a nucleotide sequence encoding a polypeptide that has a sequence homology of at least 95% with the amino acid sequence of SEQ ID NO:10 and has a polyhydroxyalkanoate synthesis activity,
    wherein the gene encoding a polyhydroxyalkanoate synthase is controlled by at least one nucleotide sequence selected from the group consisting of the following nucleotide sequences (a) or (b) in such a way that a specific activity of the polyhydroxyalkanoate synthase in cells is 0.1 U/mg-protein at most:
    (a) the nucleotide sequence of SEQ ID NO:11;
    (b) a nucleotide sequence having a sequence homology of at least 95% with the nucleotide sequence of SEQ ID NO:11 and regulating gene transcription.

2. The microorganism according to claim 1, wherein the microorganism is *Cupriavidus necator*.

3. The microorganism according to claim 1, wherein the polyhydroxyalkanoate is at least one polyester selected from the group consisting of P(3HB), P(3HB-co-3HV), and P(3HB-co-3HH).

4. A method for producing a polyhydroxyalkanoate with a weight average molecular weight of at least 4,000,000, the method comprising
    culturing in a carbon source a microorganism belonging to the genus *Cupriavidus* which is capable of producing the polyhydroxyalkanoate with a weight average molecular weight of at least 4,000,000 at a level of at least 100 g/L of productivity, the microorganism comprising
    a gene encoding a polyhydroxyalkanoate synthase having at least one nucleotide sequence selected from the group consisting of the following nucleotide sequences (1) to (4):
    (1) a nucleotide sequence encoding the amino acid sequence of SEQ ID NO:9;
    (2) a nucleotide sequence encoding a polypeptide that has a sequence homology of at least 95% with the amino acid sequence of SEQ ID NO:9 and that has a polyhydroxyalkanoate synthesis activity;
    (3) a nucleotide sequence encoding the amino acid sequence of SEQ ID NO:10; and
    (4) a nucleotide sequence encoding a polypeptide that has a sequence homology of at least 95% with the amino acid sequence of SEQ ID NO:10 and that has a polyhydroxyalkanoate synthesis activity,
    wherein the gene encoding the polyhydroxyalkanoate synthase is controlled by at least one nucleotide sequence selected from the group consisting of the following nucleotide sequences (a) or (b) in such a way that a specific activity of the polyhydroxyalkanoate synthase in cells is 0.1 U/mg-protein at most:
    (a) the nucleotide sequence of SEQ ID NO:11;
    (b) a nucleotide sequence having a sequence homology of at least 95% with the nucleotide sequence of SEQ ID NO:11 and regulating gene transcription.

5. The production method according to claim 4, wherein the carbon source comprises.

6. The production method according to claim 4, wherein the carbon source comprises at least one of a fat, an oil, and a fatty acid.

7. The microorganism according to claim 2, wherein the polyhydroxyalkanoate is at least one polyester selected from the group consisting of P(3HB), P(3HB-co-3HV), and P(3HB-co-3HH).

8. The method for producing the polyhydroxyalkanoate according to claim 4, wherein the microorganism is *Cupriavidus necator* and the polyhydroxyalkanoate is at least one polyester selected from the group consisting of P(3HB), P(3HB-co-3HV), and P(3HB-co-3HH).

9. The method for producing the polyhydroxyalkanoate according to claim 4, wherein the microorganism is *Cupriavidus necator*.

10. The method for producing the polyhydroxyalkanoate according to claim 4, wherein the polyhydroxyalkanoate is at least one polyester selected from the group consisting of P(3HB), P(3HB-co-3HV), and P(3HB-co-3HH).

11. The production method according to claim 10, wherein the carbon source comprises a sugar.

12. The production method according to claim 8, wherein the carbon source comprises a sugar.

13. The production method according to claim 9, wherein the carbon source comprises a sugar.

14. The production method according to claim 8, wherein the carbon source comprises at least one of a fat, an oil, and a fatty acid.

15. The production method according to claim 9, wherein the carbon source comprises at least one of a fat, an oil, and a fatty acid.

16. The production method according to claim 10, wherein the carbon source comprises at least one of a fat, an oil, and a fatty acid.

* * * * *

```
                         SEQUENCE LISTING

<160> NUMBER OF SEQ ID NOS: 12

<210> SEQ ID NO 1
<211> LENGTH: 25
<212> TYPE: DNA
<213> ORGANISM: Artificial
<220> FEATURE:
<223> OTHER INFORMATION: synthesized

<400> SEQUENCE: 1
ttcaattgca cgtggcagag agaca                                            25

<210> SEQ ID NO 2
<211> LENGTH: 21
<212> TYPE: DNA
<213> ORGANISM: Artificial
<220> FEATURE:
<223> OTHER INFORMATION: synthesized

<400> SEQUENCE: 2
ggaattccgg ctgccgactg g                                                21

<210> SEQ ID NO 3
<211> LENGTH: 21
<212> TYPE: DNA
<213> ORGANISM: Artificial
<220> FEATURE:
<223> OTHER INFORMATION: synthesized

<400> SEQUENCE: 3
gggcaattgg cgcaacgcaa t                                                21

<210> SEQ ID NO 4
<211> LENGTH: 21
<212> TYPE: DNA
<213> ORGANISM: Artificial
<220> FEATURE:
<223> OTHER INFORMATION: synthesized

<400> SEQUENCE: 4
tggtcacaat tgtttcctgt g                                                21

<210> SEQ ID NO 5
<211> LENGTH: 40
<212> TYPE: DNA
<213> ORGANISM: Artificial
<220> FEATURE:
<223> OTHER INFORMATION: synthesized
```

```
<400> SEQUENCE: 5
tactacaatt gcatggccct cgccggagcg ccccggagtg                             40

<210> SEQ ID NO 6
<211> LENGTH: 39
<212> TYPE: DNA
<213> ORGANISM: Artificial
<220> FEATURE:
<223> OTHER INFORMATION: synthesized

<400> SEQUENCE: 6
cactgcaatt gctggtctcc agtggtgaac ttcaaggtc                              39

<210> SEQ ID NO 7
<211> LENGTH: 30
<212> TYPE: DNA
<213> ORGANISM: Artificial
<220> FEATURE:
<223> OTHER INFORMATION: synthesized

<400> SEQUENCE: 7
cccggaattc cccgggcaag taccttgccg                                       30

<210> SEQ ID NO 8
<211> LENGTH: 59
<212> TYPE: DNA
<213> ORGANISM: Artificial
<220> FEATURE:
<223> OTHER INFORMATION: synthesized

<400> SEQUENCE: 8
cccggaattc cggctgccga ctggttgaac caggccggca gtcatgcctt ggctttgac       59

<210> SEQ ID NO 9
<211> LENGTH: 589
<212> TYPE: PRT
<213> ORGANISM: Cupriavidus necator

<400> SEQUENCE: 9
```

| Met | Ala | Thr | Gly | Lys | Gly | Ala | Ala | Ala | Ser | Thr | Gln | Glu | Gly | Lys | Ser |
|---|---|---|---|---|---|---|---|---|---|---|---|---|---|---|---|
| 1 | | | | 5 | | | | | 10 | | | | | 15 | |

| Gln | Pro | Phe | Lys | Val | Thr | Pro | Gly | Pro | Phe | Asp | Pro | Ala | Thr | Trp | Leu |
|---|---|---|---|---|---|---|---|---|---|---|---|---|---|---|---|
| | | | 20 | | | | | 25 | | | | | 30 | | |

| Glu | Trp | Ser | Arg | Gln | Trp | Gln | Gly | Thr | Glu | Gly | Asn | Gly | His | Ala | Ala |
|---|---|---|---|---|---|---|---|---|---|---|---|---|---|---|---|
| | | 35 | | | | | 40 | | | | | 45 | | | |

| Ala | Ser | Gly | Ile | Pro | Gly | Leu | Asp | Ala | Leu | Ala | Gly | Val | Lys | Ile | Ala |
|---|---|---|---|---|---|---|---|---|---|---|---|---|---|---|---|
| | 50 | | | | | 55 | | | | | 60 | | | | |

| Pro | Ala | Gln | Leu | Gly | Asp | Ile | Gln | Gln | Arg | Tyr | Met | Lys | Asp | Phe | Ser |
|---|---|---|---|---|---|---|---|---|---|---|---|---|---|---|---|
| 65 | | | | | 70 | | | | | 75 | | | | | 80 |

| Ala | Leu | Trp | Gln | Ala | Met | Ala | Glu | Gly | Lys | Ala | Glu | Ala | Thr | Gly | Pro |
|---|---|---|---|---|---|---|---|---|---|---|---|---|---|---|---|
| | | | | 85 | | | | | 90 | | | | | 95 | |

| Leu | His | Asp | Arg | Arg | Phe | Ala | Gly | Asp | Ala | Trp | Arg | Thr | Asn | Leu | Pro |
|---|---|---|---|---|---|---|---|---|---|---|---|---|---|---|---|
| | | | 100 | | | | | 105 | | | | | 110 | | |

| Tyr | Arg | Phe | Ala | Ala | Ala | Phe | Tyr | Leu | Leu | Asn | Ala | Arg | Ala | Leu | Thr |
|---|---|---|---|---|---|---|---|---|---|---|---|---|---|---|---|
| | | 115 | | | | | 120 | | | | | 125 | | | |

| Glu | Leu | Ala | Asp | Ala | Val | Glu | Ala | Asp | Ala | Lys | Thr | Arg | Gln | Arg | Ile |
|---|---|---|---|---|---|---|---|---|---|---|---|---|---|---|---|
| | 130 | | | | | 135 | | | | | 140 | | | | |

| Arg | Phe | Ala | Ile | Ser | Gln | Trp | Val | Asp | Ala | Met | Ser | Pro | Ala | Asn | Phe |
|---|---|---|---|---|---|---|---|---|---|---|---|---|---|---|---|
| 145 | | | | | 150 | | | | | 155 | | | | | 160 |

```
Leu Ala Thr Asn Pro Glu Ala Gln Arg Leu Ile Glu Ser Gly Gly
                165                 170                 175
Glu Ser Leu Arg Ala Gly Val Arg Asn Met Met Glu Asp Leu Thr Arg
            180                 185                 190
Gly Lys Ile Ser Gln Thr Asp Glu Ser Ala Phe Glu Val Gly Arg Asn
            195                 200                 205
Val Ala Val Thr Glu Gly Ala Val Val Phe Glu Asn Glu Tyr Phe Gln
        210                 215                 220
Leu Leu Gln Tyr Lys Pro Leu Thr Asp Lys Val His Ala Arg Pro Leu
225                 230                 235                 240
Leu Met Val Pro Pro Cys Ile Asn Lys Tyr Tyr Ile Leu Asp Leu Gln
                245                 250                 255
Pro Glu Ser Ser Leu Val Arg His Val Glu Gln Gly His Thr Val
            260                 265                 270
Phe Leu Val Ser Trp Arg Asn Pro Asp Ala Ser Met Ala Gly Ser Thr
        275                 280                 285
Trp Asp Asp Tyr Ile Glu His Ala Ala Ile Arg Ala Ile Glu Val Ala
        290                 295                 300
Arg Asp Ile Ser Gly Gln Asp Lys Ile Asn Val Leu Gly Phe Cys Val
305                 310                 315                 320
Gly Gly Thr Ile Val Ser Thr Ala Leu Ala Val Leu Ala Ala Arg Gly
                325                 330                 335
Glu His Pro Ala Ala Ser Val Thr Leu Leu Thr Thr Leu Leu Asp Phe
            340                 345                 350
Ala Asp Thr Gly Ile Leu Asp Val Phe Val Asp Glu Gly His Val Gln
        355                 360                 365
Leu Arg Glu Ala Thr Leu Gly Gly Gly Ala Gly Ala Pro Cys Ala Leu
    370                 375                 380
Leu Arg Gly Leu Glu Leu Ala Asn Thr Phe Ser Phe Leu Arg Pro Asn
385                 390                 395                 400
Asp Leu Val Trp Asn Tyr Val Val Asp Asn Tyr Leu Lys Gly Asn Thr
                405                 410                 415
Pro Val Pro Phe Asp Leu Leu Phe Trp Asn Gly Asp Ala Thr Asn Leu
            420                 425                 430
Pro Gly Pro Trp Tyr Cys Trp Tyr Leu Arg His Thr Tyr Leu Gln Asn
        435                 440                 445
Glu Leu Lys Val Pro Gly Lys Leu Thr Val Cys Gly Val Pro Val Asp
    450                 455                 460
Leu Ala Ser Ile Asp Val Pro Thr Tyr Ile Tyr Gly Ser Arg Glu Asp
465                 470                 475                 480
His Ile Val Pro Trp Thr Ala Ala Tyr Ala Ser Thr Ala Leu Leu Ala
                485                 490                 495
Asn Lys Leu Arg Phe Val Leu Gly Ala Ser Gly His Ile Ala Gly Val
            500                 505                 510
Ile Asn Pro Pro Ala Lys Asn Lys Arg Ser His Trp Thr Asn Asp Ala
        515                 520                 525
Leu Pro Glu Ser Pro Gln Gln Trp Leu Ala Gly Ala Ile Glu His His
    530                 535                 540
Gly Ser Trp Trp Pro Asp Trp Thr Ala Trp Leu Ala Gly Gln Ala Gly
545                 550                 555                 560
Ala Lys Arg Ala Ala Pro Ala Asn Tyr Gly Asn Ala Arg Tyr Arg Ala
                565                 570                 575
Ile Glu Pro Ala Pro Gly Arg Tyr Val Lys Ala Lys Ala
```

-continued

```
                580                 585

<210> SEQ ID NO 10
<211> LENGTH: 594
<212> TYPE: PRT
<213> ORGANISM: Aeromonas caviae

<400> SEQUENCE: 10

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365
```

```
Ala Ala Leu Glu Ala Gln Asn Glu Ala Lys Gly Ile Met Asp Gly Arg
        370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
    530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 11
<211> LENGTH: 263
<212> TYPE: DNA
<213> ORGANISM: Cupriavidus necator

<400> SEQUENCE: 11
gcatggccct cgccggagcg ccccggagtg gcgtcacagc cgctcccgtg tatcgccagc      60
aacgttgttt gtgcattgca caaaatccac ttgacattgg atctggcgcc cctaaaatag     120
gaattgttgc ggcgcaccaa ataagaaatg cgccttgacc cacccacacg cctgggctgg     180
ccgaatcggg cacaacaccg tcacggccct gacatctagg cggcttaatt tgctagacct     240
tgaagttcac cactggagac cag                                             263

<210> SEQ ID NO 12
<211> LENGTH: 117
<212> TYPE: DNA
<213> ORGANISM: Escherichia coli

<400> SEQUENCE: 12
gcgcaacgca attaatgtga gttagctcac tcattaggca ccccaggctt tacactttat      60
gcttccggct cgtatgttgt gtggaattgt gagcggataa caatttcaca caggaaa        117
```